United States Patent
Kim et al.

(10) Patent No.: US 11,262,566 B2
(45) Date of Patent: Mar. 1, 2022

(54) BIOLOGICAL TISSUE INSPECTION DEVICE AND METHOD THEREFOR

(71) Applicant: KOH YOUNG TECHNOLOGY INC., Seoul (KR)

(72) Inventors: Hong Ki Kim, Yongin-si (KR); Min Kyu Kim, Gwangmyeong-si (KR); Min Young Hwangbo, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 0 days.

(21) Appl. No.: 16/916,801

(22) Filed: Jun. 30, 2020

(65) Prior Publication Data

US 2020/0348499 A1 Nov. 5, 2020

Related U.S. Application Data

(63) Continuation of application No. 16/301,307, filed as application No. PCT/KR2017/004944 on May 12, 2017, now Pat. No. 10,754,134.

(30) Foreign Application Priority Data

May 13, 2016 (KR) .......................... 10-2016-0058962

(51) Int. Cl.
    *G02B 21/00* (2006.01)
    *G02B 21/02* (2006.01)
    (Continued)

(52) U.S. Cl.
    CPC ............. *G02B 21/0012* (2013.01); *A61B 5/00* (2013.01); *A61B 5/0062* (2013.01);
    (Continued)

(58) Field of Classification Search
    CPC .... G02B 21/0012; G02B 21/02; G02B 27/14; G02B 21/025; G02B 21/14; G02B 21/26;
    (Continued)

(56) References Cited

U.S. PATENT DOCUMENTS 9,557,549 B2 * 1/2017 Yaqoob ................ G01N 21/453
2002/0131165 A1 9/2002 Takahama
(Continued)

FOREIGN PATENT DOCUMENTS

CN 1375719 10/2002
CN 103868895 6/2014
(Continued)

OTHER PUBLICATIONS

Chinese Office Action, with English translation, corresponding to Chinese Application or Patent No. 201780005393.7, dated Dec. 3, 2020.
(Continued)

*Primary Examiner* — Tracy Y. Li
(74) *Attorney, Agent, or Firm* — Kile Park Reed & Houtteman PLLC

(57) ABSTRACT

A biological tissue inspection apparatus is disclosed. The biological tissue inspection apparatus comprises a stage and a probe. The probe comprises an optical imaging device, an optical interference detector, and a light guide. The probe acquires data regarding optical images and optical interference, through the optical imaging device and the optical interference detector. The stage or the probe moves such that a selected area of the inspection object is positioned in the FOV of the optical imaging device and of the optical interference detector. The light guide is configured such that illumination light from the optical imaging device and measurement light from the optical interference detector are coaxially emitted to the inspection object.

20 Claims, 11 Drawing Sheets

(51) Int. Cl.

| | | |
|---|---|---|
| *G01N 21/45* | (2006.01) | |
| *A61B 5/00* | (2006.01) | |
| *G02B 27/14* | (2006.01) | |
| *G01B 7/04* | (2006.01) | |
| *A61B 90/00* | (2016.01) | |
| *G02B 21/14* | (2006.01) | |
| *G02B 21/26* | (2006.01) | |
| *G02B 21/36* | (2006.01) | |
| *G06T 7/00* | (2017.01) | |

(52) U.S. Cl.
CPC ............ *A61B 90/361* (2016.02); *A61B 90/37* (2016.02); *G01B 7/046* (2013.01); *G01N 21/45* (2013.01); *G02B 21/02* (2013.01); *G02B 21/025* (2013.01); *G02B 21/14* (2013.01); *G02B 21/26* (2013.01); *G02B 21/368* (2013.01); *G02B 27/14* (2013.01); *G06T 7/0012* (2013.01); *A61B 5/0037* (2013.01); *A61B 5/0066* (2013.01); *A61B 5/0073* (2013.01); *A61B 5/7425* (2013.01); *A61B 2090/3618* (2016.02); *G06T 2207/10056* (2013.01); *G06T 2207/10152* (2013.01); *G06T 2207/20104* (2013.01); *G06T 2207/30024* (2013.01); *G06T 2207/30096* (2013.01)

(58) Field of Classification Search
CPC .... G02B 21/368; G02B 27/141; G01N 21/45; A61B 5/00; A61B 5/0062; A61B 90/361; A61B 90/37; A61B 5/0073; A61B 5/7425; A61B 5/0037; A61B 5/0066; A61B 2090/3618; A61B 5/0059; G01B 7/046; G06T 7/0012; G06T 2207/10056; G06T 2207/10152; G06T 2207/20104; G06T 2207/30024; G06T 2207/30096
See application file for complete search history.

(56) References Cited

U.S. PATENT DOCUMENTS

| | | | |
|---|---|---|---|
| 2007/0195330 A1* | 8/2007 | Ohashi | ............... A61B 5/14551 356/498 |
| 2008/0062429 A1 | 3/2008 | Liang et al. | |
| 2008/0118886 A1 | 5/2008 | Liang et al. | |
| 2009/0185191 A1 | 7/2009 | Boppart et al. | |
| 2010/0208204 A1 | 8/2010 | Imamura et al. | |
| 2011/0007324 A1 | 1/2011 | Suzuki et al. | |
| 2011/0080560 A1 | 4/2011 | Imamura et al. | |
| 2011/0228218 A1 | 9/2011 | Hauger et al. | |
| 2011/0267584 A1 | 11/2011 | Imamura et al. | |
| 2012/0001069 A1 | 1/2012 | Kashihara | |
| 2013/0057827 A1 | 3/2013 | Imamura et al. | |
| 2013/0130307 A1* | 5/2013 | Sugiyama | .......... G06K 9/00147 435/34 |
| 2013/0182096 A1 | 7/2013 | Boccara et al. | |
| 2013/0293838 A1 | 11/2013 | Makihira et al. | |
| 2014/0024949 A1 | 1/2014 | Wei et al. | |
| 2014/0163388 A1 | 6/2014 | Sasayama et al. | |
| 2015/0057972 A1 | 2/2015 | Kitamura et al. | |
| 2015/0077707 A1 | 3/2015 | Hauger et al. | |
| 2015/0077708 A1 | 3/2015 | Hauger et al. | |
| 2015/0285619 A1 | 10/2015 | Motohashi et al. | |
| 2015/0313466 A1 | 11/2015 | Yoshida | |
| 2016/0081545 A1 | 3/2016 | Hauger et al. | |
| 2016/0161730 A1* | 6/2016 | Nakamura | .......... G02B 21/362 356/498 |
| 2016/0198961 A1 | 7/2016 | Homyk et al. | |
| 2016/0302738 A1 | 10/2016 | Yoshida et al. | |
| 2016/0310024 A1 | 10/2016 | Yoshida et al. | |
| 2017/0188819 A1 | 7/2017 | Hauger et al. | |
| 2017/0188820 A1 | 7/2017 | Hauger et al. | |
| 2018/0283846 A1* | 10/2018 | Katashiba | .......... G01B 9/02058 |
| 2019/0196163 A1 | 6/2019 | Kim et al. | |
| 2020/0348499 A1 | 11/2020 | Kim et al. | |

FOREIGN PATENT DOCUMENTS

| | | |
|---|---|---|
| JP | 2001-215109 | 8/2001 |
| JP | 2009-109787 | 5/2009 |
| JP | 2010-035607 | 2/2010 |
| JP | 2010-509993 | 4/2010 |
| JP | 2011-21902 | 2/2011 |
| JP | 2013-137541 | 7/2013 |
| JP | 2013-183873 | 9/2013 |
| JP | 2013-184018 | 9/2013 |
| JP | 2013-212313 | 10/2013 |
| JP | 2014-121647 | 7/2014 |
| JP | 2014-523537 | 9/2014 |
| JP | 2014-533996 | 12/2014 |
| JP | 2015-040825 | 3/2015 |
| JP | 2015-200578 | 11/2015 |
| JP | 6806797 | 12/2020 |
| KR | 10-2008-0001910 | 1/2008 |
| KR | 10-2009-0030567 | 3/2009 |
| KR | 10-2009-0078296 | 7/2009 |
| KR | 10-2012-0097237 | 9/2012 |
| WO | 2013/056006 | 4/2013 |

OTHER PUBLICATIONS

Office Action from Intellectual Property of India corresponding to India Application No. 201817044438, dated Dec. 16, 2020.
Korean Office Action with English Translation corresponding to Korean Application No. 10-2018-0049977, dated Jul. 16, 2021.
International Search Report for International Application No. PCT/KR2017/004944, dated Aug. 16, 2017.
Written Opinion with English Translation for International Application No. PCT/KR2017/004944, dated Aug. 16, 2017.
Korean Office Action with English translation for Korean Application No. 10-2016-0058962, dated Jul. 17, 2017.
Chinese Office Action with English Translation for Chinese Application or Patent No. 201820993058.4; dated Nov. 27, 2018.
Supplementary European Search Report for European Application No. 17 79 6423, dated Apr. 1, 2019.
Japanese Office Action for Japanese Application No. 2018-560022, with English translation, dated Oct. 29, 2019.
Extended European Search Report for Application No./Patent No. 21165794.5 dated Sep. 6, 2021.
Japanese Office Action with English translation for Japanese Patent Application No. 2020-201855, dated Nov. 9, 2021.

\* cited by examiner

BIOLOGICAL TISSUE INSPECTION DEVICE AND METHOD THEREFOR

CROSS-REFERENCE TO RELATED APPLICATIONS

This application is a continuation application of U.S. patent application Ser. No. 16/301,307, filed Nov. 13, 2018, the disclosure of which is herein incorporated by reference in its entirety. The U.S. patent application Ser. No. 16/301,307 is a national entry of International Application No. PCT/KR2017/004944, filed on May 12, 2017, which claims priority to Korean Application No. 10-2016-0058962 filed on May 13, 2016, respectively, the entire contents of which are incorporated herein by reference.

TECHNICAL FIELD

The present disclosure relates to a biological tissue inspection apparatus, and more specifically, to a biological tissue inspection apparatus and method for inspecting biological tissue using optical technology.

BACKGROUND ART

In order to diagnose diseases occurring in a human body, tissue inspection, in which tissue of an area suspected of diseases is extracted and examined to diagnose diseases, is used.

For the tissue inspection, tissue is extracted using a method such as cell aspiration, gun biopsy, incisional biopsy, or excisional biopsy, and then the extracted tissue sample is sliced to produce a slide, dyed, and then observed with a microscope. In the process of producing a slide, an extracted tissue sample is hardened by fixation, dehydrating, etc., then sliced, dyed, and covered with a cover glass.

After the slide is produced in this manner, a physician in charge of pathological diagnosis and judgment can observe the tissue slide through a microscope and make an accurate diagnosis decision.

Modern people suffer from various diseases, and a variety of diseases including cancer are being treated by a surgical procedure to extract a problematic organ. However, when a surgery is performed for the extraction, the position and range of a target area to be extracted, such as tumor tissue in an organ or lesion of a human body, is usually determined by the naked eye and experience of the operating surgeon. Therefore, determining the range of the tumor tissue for extraction is limited to the range that is observable by the physician with the naked eye, and it is difficult to determine whether or not a small region that is too small to be observable with the naked eye corresponds to a tumor. As a result, for example, when tumor tissue is extracted for cancer surgery, in order to prevent the tumor from remaining, it is normally necessary to extract a region that is wider than the tumor tissue observed by the naked eye, causing an additional burden on the patient's recovery. There is still a problem that it is impossible to identify a tumor that is not exposed to the surface, despite removing a larger area than the tumor tissue.

It may be dangerous to extract an area larger than an actual extraction target. For example, when performing a thyroidectomy, the parathyroid gland, which perform functions such as calcium metabolism or hormone secretion, should not be excised from a functional perspective. However, it is not easy to clearly distinguish between normal thyroid tissue, a parathyroid gland, lymph, or removable adipose tissue with the naked eye. In such a case, it is impossible to perform a surgery in which the portion including the tumor is widely extracted as in the above-described method of cancer tissue extraction.

In order to solve the problems described above, the above-described tissue inspection is used to understand what kind of tissue the extracted tissue corresponds to and in what condition it is. However, tissue inspections that are generally used often take more than a few days in order to understand the result thereof due to a process of fixing the tissue sample by a fixation fluid in order to produce a slide, the congestion of pathologic inspection, or the like. Thus, it is difficult to use such tissue inspections in order to make a decision on the tissue during surgery. In a frozen specimen inspection or frozen slice inspection that is used in order to solve these problems, tissue is frozen rather than being fixed, and a slide is produced by slicing the frozen tissue. However, this process takes at least 30 minutes, which is a great burden for both the surgeon and the patient.

SUMMARY

The present disclosure has been made in order to solve the technical problems as described above. More specifically, an object of the present disclosure is to provide a biological tissue inspection apparatus and method in order to observe target tissue and make a determination quickly during surgery in case it is necessary to urgently perform tissue inspection during the surgery.

A biological tissue inspection apparatus according to an embodiment of the present disclosure includes a stage on which an inspection object is loaded, and a probe configured to obtain an optical image of the inspection object and obtain optical interference data about the inspection object of an area that is selected from the optical image, and the probe or the stage is movable to obtain the optical interference data about the inspection object of the selected area.

In the biological tissue inspection apparatus according to an embodiment of the present disclosure, the probe includes an optical imaging device configured to obtain the optical image, an optical interference detector configured to obtain the optical interference data, and a light guide configured to form a first light path along which illumination light is emitted from an illumination light source, reflected from the inspection object, and guided to the optical imaging device to obtain the optical image, and form a second light path by causing measurement light to be incident on the inspection object to obtain the optical interference data.

In the biological tissue inspection apparatus according to an embodiment of the present disclosure, the illumination light source is provided in the probe.

In the biological tissue inspection apparatus according to an embodiment of the present disclosure, the illumination light source is provided outside the probe separately from the probe.

In the biological tissue inspection apparatus according to an embodiment of the present disclosure, the light guide includes a light path controller, and the first light path and the second light path coaxially overlap with each other in a section between the light path controller and the inspection object.

In the biological tissue inspection apparatus according to an embodiment of the present disclosure, the light path controller is a semi-transmissive mirror, and the semi-transmissive mirror allows the illumination light to pass therethrough and refracts the measurement light, or refracts the illumination light and reflects the measurement light.

In the biological tissue inspection apparatus according to an embodiment of the present disclosure, the light guide includes a magnification changer, the magnification changer includes a variable magnification objective lens, and the first light path and the second light path pass through the variable magnification objective lens.

In the biological tissue inspection apparatus according to an embodiment of the present disclosure, the light guide includes a magnification changer, the magnification changer includes a plurality of fixed magnification objective lenses, and the first light path and the second light path pass through one of the plurality of the fixed magnification objective lenses.

In the biological tissue inspection apparatus according to an embodiment of the present disclosure, the optical interference detector further includes an interference light source configured to project near-infrared light, a beam splitter for optical interference measurement configured to separate the near-infrared light from the interference light source into the measurement light and reference light, and a reference mirror configured to reflect the reference light.

In the biological tissue inspection apparatus according to an embodiment of the present disclosure, the reference mirror is configured to move based on a thickness of the fixed magnification objective lens through which the second light path passes.

In the biological tissue inspection apparatus according to an embodiment of the present disclosure, the probe further includes a guide beam projector configured to project a guide beam such that a projection point of the guide beam is located within a Field Of View (FOV) of the optical imaging device, the optical imaging device obtains the optical image such that the projection point of the guide beam is visually identified in the optical image, and the projection point of the guide beam is included in the selected area.

In the biological tissue inspection apparatus according to an embodiment of the present disclosure, the guide beam projector projects the guide beam along the second light path.

In the biological tissue inspection apparatus according to an embodiment of the present disclosure, a position of the probe or the stage is adjustable on a z-axis such that a surface of the inspection object is located within a measurement range in a z-axis direction of the optical interference detector.

In the biological tissue inspection apparatus according to an embodiment of the present disclosure, the position of the probe or the stage is adjusted on the z-axis after the optical interference detector obtains the optical interference data of the inspection object in the selected area.

In the biological tissue inspection apparatus according to an embodiment of the present disclosure, the position of the probe or the stage is adjusted on the z-axis simultaneously with the optical interference detector obtaining the optical interference data of the inspection object in the selected area.

In the biological tissue inspection apparatus according to an embodiment of the present disclosure, the probe further includes a distance measurement device configured to measure a distance between the probe and the surface of the inspection object, and the position of the probe or the stage on the z-axis is adjusted based on the distance measured by the distance measurement device.

In the biological tissue inspection apparatus according to an embodiment of the present disclosure, a position of the probe or the stage is adjustable on a x-axis, on a y-axis, or on the x-axis and the y-axis such that the selected area is included within a FOV of the optical imaging device or a FOV of the optical interference detector.

In the biological tissue inspection apparatus according to an embodiment of the present disclosure, the biological tissue inspection apparatus further includes a display configured to display the optical image, and an input device configured to receive a user selection for selecting a partial area of the optical image.

In the biological tissue inspection apparatus according to an embodiment of the present disclosure, the biological tissue inspection apparatus further includes a transceiver configured to sent out the optical image, the optical interference data, or the optical image, and the optical interference data such that the optical image, the optical interference data, or the optical image and the optical interference data can be shared in real time.

A biological tissue inspection method according to an embodiment of the present disclosure using a biological tissue inspection apparatus including a stage and a probe comprises the steps of: obtaining, by the biological tissue inspection apparatus, an optical image of an inspection object; selecting an area of the optical image; and obtaining optical interference data about the inspection object of the selected area of the optical image, and the probe or the stage is movable to obtain the optical interference data about the inspection object of the selected area.

In the biological tissue inspection method according to an embodiment of the present disclosure, the probe includes an optical imaging device and an optical interference detector, and the biological issue inspection method further includes the step of adjusting a position of the probe or the stage on a z-axis such that a surface of the inspection object is included within a measurement range in a z-axis direction of the optical interference detector.

In the biological tissue inspection method according to an embodiment of the present disclosure, the adjusting the position of the probe or the stage on the z-axis is performed after the obtaining the optical interference data about the inspection object of the selected area.

In the biological tissue inspection method according to an embodiment of the present disclosure, the adjusting the position of the probe or the stage on the z-axis is performed simultaneously with the obtaining the optical interference data about the inspection object of the selected area.

In the biological tissue inspection method according to an embodiment of the present disclosure, the probe includes an optical imaging device and an optical interference detector, and the biological tissue inspection method further includes the step of adjusting a position of the probe or the stage on a x-axis, a y-axis, or the x-axis and the y-axis such that the selected area is included within a FOV (Field of View) of the optical imaging device or the optical interference detector.

In the biological tissue inspection method according to an embodiment of the present disclosure, the biological tissue inspection method further includes the step of changing a magnification for the probe to obtain the optical image or the optical interference data.

In the biological tissue inspection method according to an embodiment of the present disclosure, the biological tissue inspection method further includes the step of correcting the color of the optical image.

The inspection apparatus and method according to the present disclosure assist a physician to accurately determine the area of tissue subject to surgery, such as an extraction operation, in real time during surgery, so that the speed, accuracy, and safety of the operation can be improved.

Through the inspection apparatus and method according to the present disclosure, it is possible to check an optical image of an inspection object, and quickly select an area on which tissue inspection is to be performed.

Through the inspection apparatus and method according to the present disclosure, it is possible to perform tissue inspection in real time without performing a conventional biopsy procedure such as slide production. In a thyroid surgery, since there is no need to excise a wide range, it is possible to protect the parathyroid glands.

DETAILED DESCRIPTION

Hereinafter, a biological tissue inspection apparatus and method according to the present disclosure will be described with reference to embodiments.

Biological Tissue Inspection Apparatus

Figure 1:
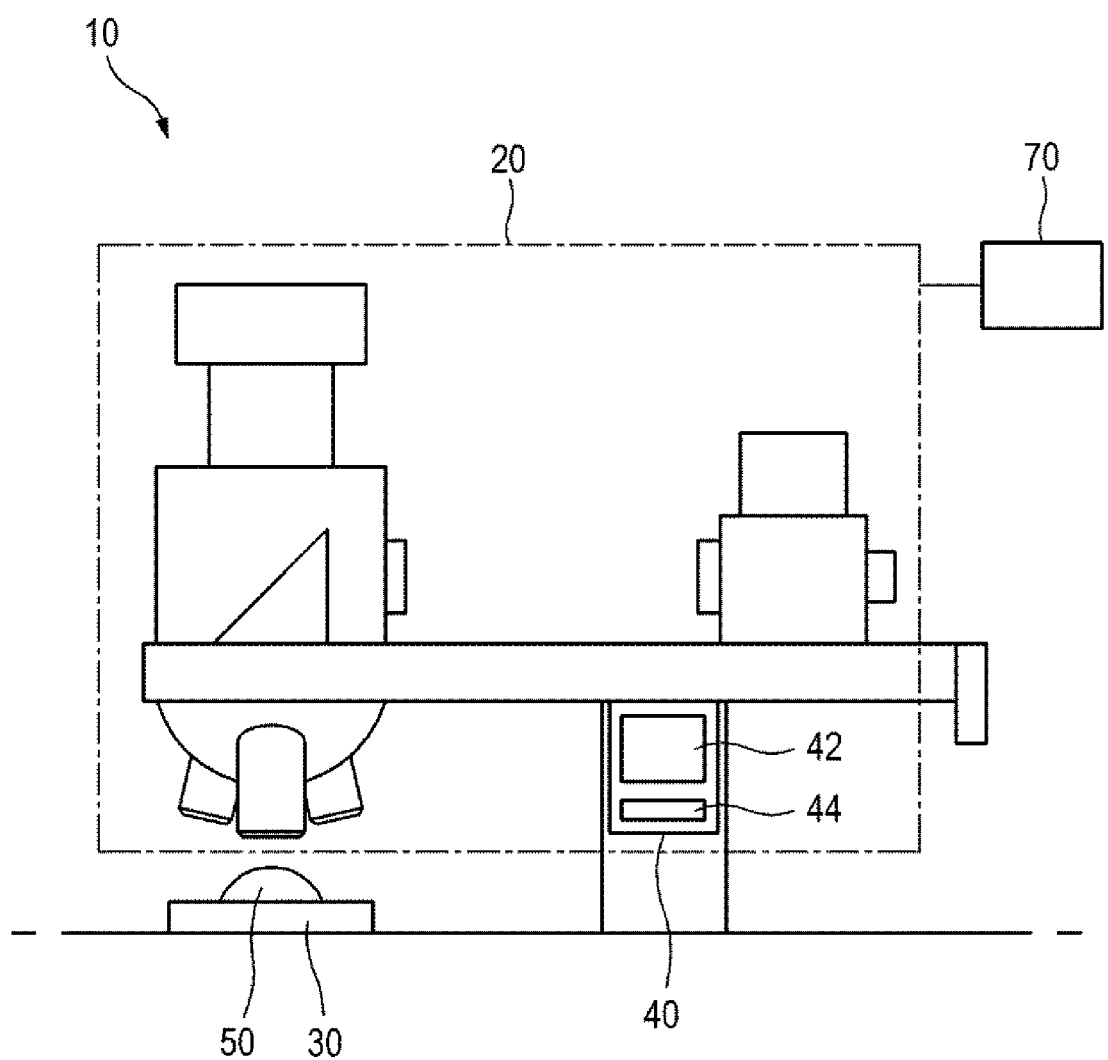
FIG. 1 is a structural view showing a biological tissue inspection apparatus according to the present disclosure.

FIG. 1 illustrates a biological tissue inspection apparatus according to an embodiment of the present disclosure. The biological tissue inspection apparatus 10 according to an embodiment of the present disclosure includes a probe 20 and a stage 30. Biological tissue 50 to be examined is loaded on the stage 30 and the probe 20 obtains an optical image and optical interference data about the inspection object through an objective lens arranged on the inspection object side. The biological tissue inspection apparatus 10 may further include an area selector 40. The area selector 40 may provide a selection interface to a user to obtain the optical interference data of a specific area desired by the user.

Probe

Figure 2:
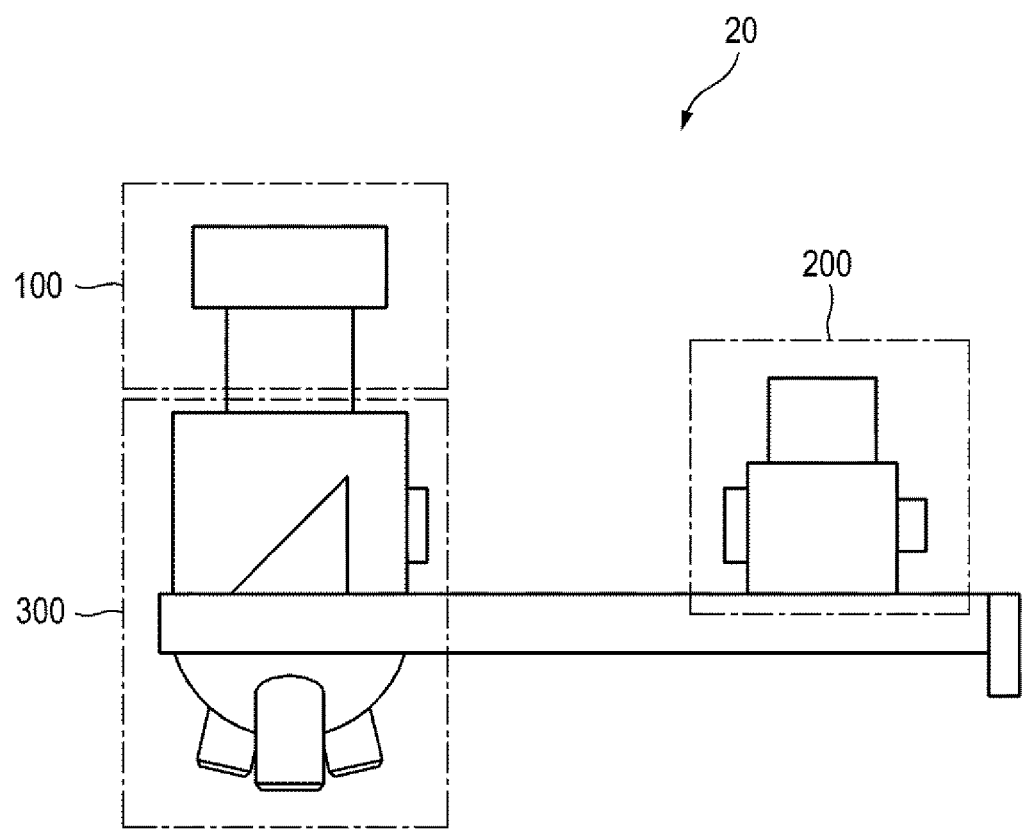
FIG. 2 illustrates a probe of the biological tissue inspection apparatus according to the present disclosure.

FIG. 2 illustrates the configuration of the probe 20. The probe 20 includes an optical imaging device 100 configured to obtain the optical image of the inspection object, an optical interference detector 200 configured to obtain optical interference data for the inspection object, and a light guide 300 configured to guide illumination light and measurement light such that the optical imaging device 100 and the optical interference detector 200 can obtain the optical image and optical interference data of the inspection object 50.

Optical Imaging Device

Figure 3:
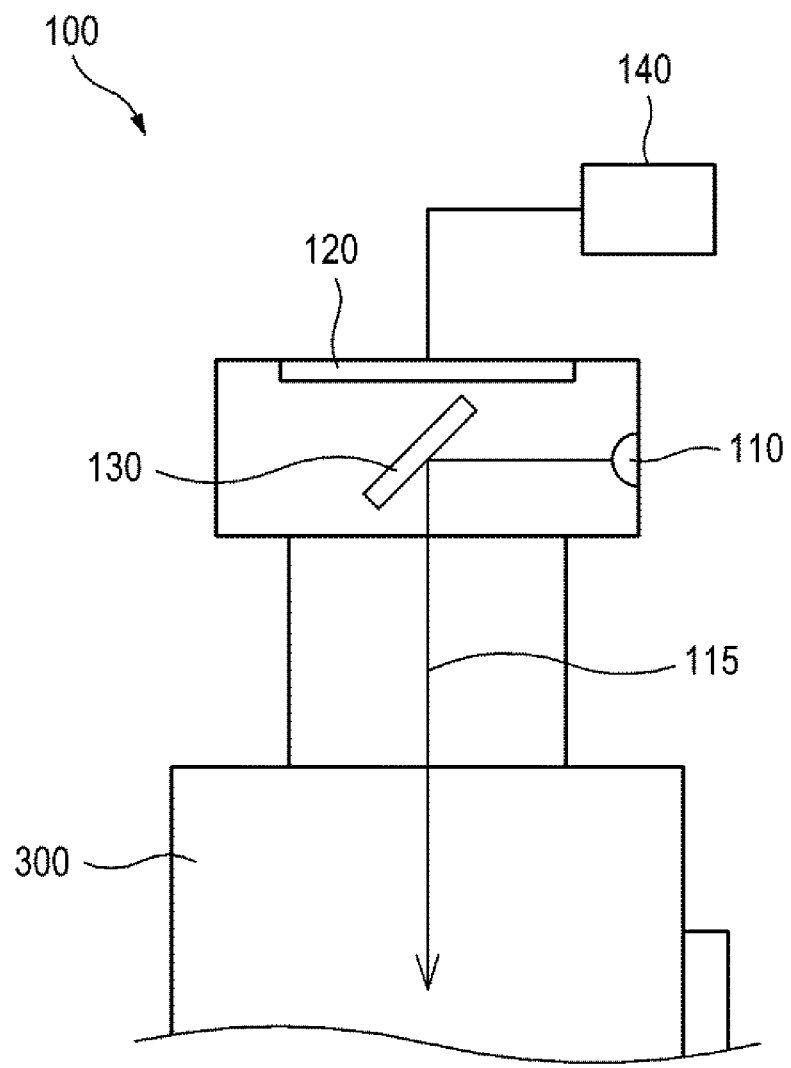
FIG. 3 illustrates an optical imaging device of the probe of the biological tissue inspection apparatus according to the present disclosure.

The optical imaging device 100 illustrated in FIG. 3 obtains the optical image of the inspection object 50. The optical image may be a general two-dimensional image of the inspection object, but it is also possible to obtain other images, for example, a three-dimensional image, if necessary. Hereinafter, for ease of explanation, it is described that the optical imaging device 100 obtains a general two-dimensional image.

As illustrated in FIG. 3, the optical imaging device 100 includes an illumination light source 110 configured to emit the illumination light 115 to the inspection object so as to improve image quality, and a light sensor 120 configured to sense light reflected from the inspection object and convert the light into an electrical signal. When the illumination light source 110 is attached to a side surface of the light sensor 120 as illustrated in FIG. 3, the direction of the illumination light 115 is turned toward the inspection object 50 through a beam splitter 130 so that the illumination light 115 can be projected onto the inspection object through the light guide 300. After being reflected from the inspection object, the illumination light 115 may pass through the light guide 300 and then reach the light sensor 120.

Meanwhile, the path of the illumination light 115 described above is only one example. As another example, the illumination light 115 may be projected straightly to the inspection object through the light guide 300. Alternatively, as will be described below with reference to FIG. 7, a separate external illumination light source 170 is disposed, and the external illumination light source 170 may project illumination light to the inspection object 50 without passing through the light guide 300.

The illumination light 115 projected by the illumination light source 110 may be a visible light beam. The light sensor 120 may be a CCD image sensor or a CMOS image sensor capable of sensing light in a visible light range. The light sensor 120 may convert the sensed light into an electrical signal and may transmit the electrical signal to a processor 140. The processor 140 may generate an image of the inspection object 50 based on the electric signal delivered from the light sensor 120.

The optical image of the inspection object 50 itself, obtained by the optical imaging device 100, may be utilized as material for observing the inspection object. The optical image may also be utilized for movement and operation of the stage 30 and the probe 20. The optical image may also be used to identify an area to be measured by the optical interference detector 200.

In an embodiment of the present disclosure, the optical image may be provided to the area selector 40. As will be described later, a user may select an area to be checked through the area selector 40. The biological tissue inspection apparatus 10 can obtain optical interference data for the area selected by the user.

In the foregoing, the optical imaging device has been described as having a configuration for obtaining a two-dimensional image of the surface of the inspection object using visible light as a light source, as an example. However, if necessary, the optical imaging device may include a configuration for capturing an optical image necessary to generate a three-dimensional image. For example, as a method of generating a three-dimensional image based on binocular parallax, it is possible to generate a three-dimensional image by synthesizing two-dimensional images obtained with a predetermined angle difference with respect to the inspection object. In order to obtain a three-dimensional image in this manner, the optical imaging device may include two cameras arranged with a predetermined angle difference with respect to the inspection object. Alternatively, the optical imaging device may include a camera and a transfer device capable of moving the camera. In this case, as the camera is moved by the transfer device, it is possible to obtain two-dimensional images of the inspection object from different angles. Alternatively, it is also possible to generate a three-dimensional image of the inspection object using pattern light. That is, a method of projecting pattern light with constant period while changing the phase of the pattern light, obtaining an image of a pattern formed by phase-shifted pattern light on the inspection object, and then processing the pattern image so as to generate a three-dimensional image of the inspection object, may be applied to the inspection device according to the present disclosure. In order to apply such a method, the optical imaging device may further include a pattern light projector for projecting the pattern light, a camera for obtaining an image formed by the pattern light on the inspection object, and a processor for generating a three-dimensional image from the measured pattern image.

Optical Interference Detector

Figure 4:
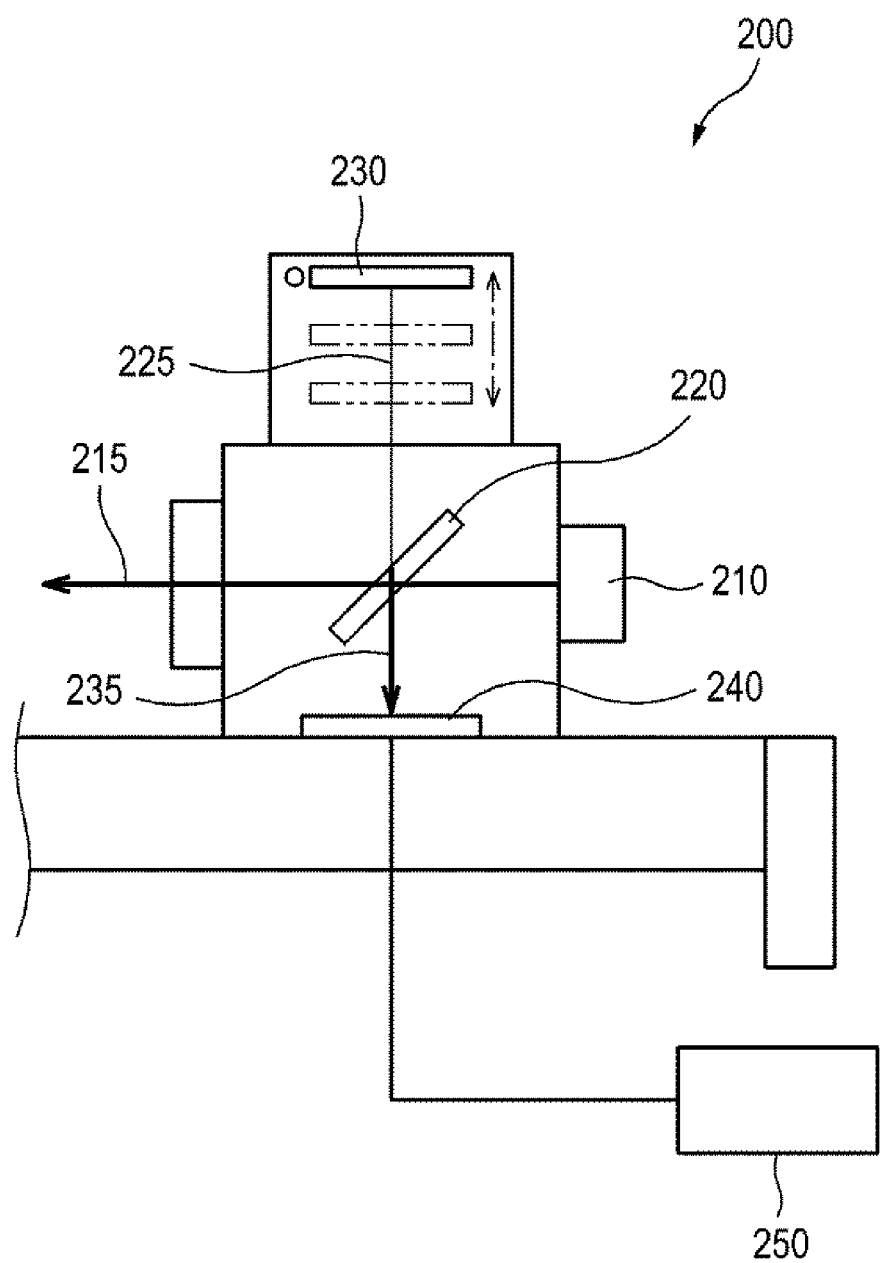
FIG. 4 illustrates an optical interference detector of the biological tissue inspection apparatus according to the present disclosure.

The optical interference detector 200 may obtain optical interference data in order to generate a three-dimensional image for all or part of the inspection object. The optical interference detector 200 may also obtain optical interference data for a specific area of the inspection object selected by the user. FIG. 4 illustrates a case where, for example, a Michelson-type interferometer is used as the optical interference detector 200. The optical interference detector 200 may include an interference light source 210 configured to project near-infrared light, a beam splitter 220 configured to separate the near-infrared light from the interference light source 210 into the measurement light 215 and the reference light 225, a reference mirror 230 configured to reflect the reference light separated by the beam splitter 220, and an interference light sensor 240 configured to generate optical interference data by sensing the interference light formed by the measurement light 215 and the reference light 225. The optical interference detector 200 may also include a processor 250 configured to generate a three-dimensional image from the optical interference data.

The interference light source 210 may project light while tuning the wavelength of the light so as to take tomographic images of human tissue by depth. As the light used for imaging the inspection object in the optical interference measurement, a laser having a wavelength in the infrared range of 750 to 1300 nm may be used. Specifically, the longer the wavelength, the deeper the depth of the human tissue that can be penetrated. Therefore, instead of projecting only a laser with a single wavelength, the interference light source may project the laser light while changing the wavelength from a shorter wavelength to a longer wavelength in order to obtain a stereoscopic interference signal up to a predetermined depth from the surface of the inspection object 50.

The measurement light 215, separated by the beam splitter 220, may be subjected to a path change by the light guide 300, which will be described later, so as to be projected onto the inspection object 50 loaded on the stage 30. The measurement light 215 projected onto the inspection object 50 is reflected from the surface of the inspection object 50, or penetrates the surface to a certain depth depending on the wavelength of the measurement light 215 and is then scattered back. Thereafter, the reflected measurement light or the back-scattered measurement light returns to the optical interference detector 200 via an opposite path. The measurement light 215 and the reference light 225 are superposed at the beam splitter 220 to form interference light 235, and the interference light 235 formed is detected by the interference light sensor 240. The interference light sensor 240 generates optical interference data from the interference light and transmits optical interference data to the processor 250. The processor 250 may generate tomographic images of the inspection object 50 from the optical interference data, thereby generating a three-dimensional image of the inspection object 50 from the tomographic images. For description purposes, both the interference light sensor 240 and the processor 250 have been illustrated as being included in the optical interference detector 200. However, each of the interference light sensor 240 and the processor 250 may be separated from the optical interference detector 200 and may be connected to the optical interference detector 200 via communication means such as an optical cable.

The beam splitter 220 separates the light from the interference light source 210 into measurement light 215 and reference light 225. As described above, the measurement light 215 is projected onto the inspection object 50 via the light guide 300 and reflected from the surface of the inspection object 50, or the measurement light 215 penetrates the surface to a certain depth, is scattered back, and then returned to the optical interference detector 200. The reference light is reflected by the reference mirror 230 to return to the beam splitter 220 again, and interferes with the measurement light 215 that is returned to the optical interference detector to form interference light 235. The interference light formed is detected by the interference light sensor 240.

The reference mirror 230 reflects the reference light 225 separated by the beam splitter 220 such that the reference light forms the interference light 235 together with the measurement light 215 reflected or scattered back from the inspection object 50. At that time, since the path difference between the measurement light 215 and the reference light 225 can be detected by the interference light sensor 240 when the path difference is within a coherence length of the light projected by the interference light source 210, the position of the reference mirror 230 may be moved in order to properly adjust the path difference. Details related to this will be described later.

Light Guide

Figure 5:
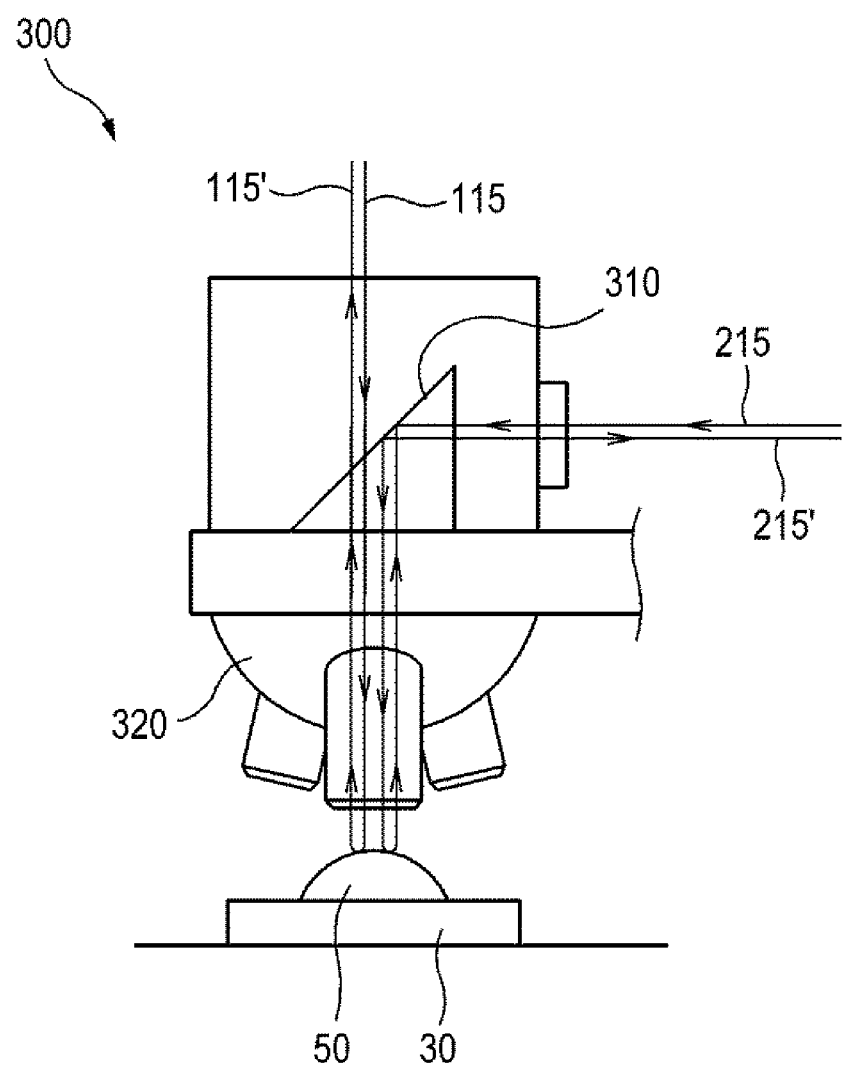
FIG. 5 illustrates a light guide of the biological tissue inspection apparatus according to the present disclosure.

The light guide 300 illustrated in FIG. 5 may perform a function of guiding the illumination light 115 from the optical imaging device 100, the measurement light 215 from the optical interference detector 200, or both the illumination light 115 and the measurement light 215 to the inspection object 50 on the stage 30. The light guide 300 may include a light path controller 310 and a magnification changer 320.

The light path controller 310 may control the path of the illumination light 115, the measurement light 215, or both the illumination light 115 and the measurement light 215. The illumination light 115 and the measurement light 215 are incident on the light guide 300 and reach the light path controller 310 as described above. As illustrated in FIG. 5, the light path controller 310 may transmit the illumination light 115 as it is to project the illumination light 115 onto the inspection object. Further, the light path controller may project the measurement light 215 onto the inspection object 50 by adjusting the path of the measurement light such that the measurement light 215 becomes coaxial with the illumination light 115. In addition, the illumination light 115' and the measurement light 215' reflected or scattered back from the inspection object 50 may be returned to the optical imaging device 100 and the optical interference detector 200, respectively, so as to obtain the optical image and optical interference data.

As the light path controller 310, a semi-transmissive mirror such as a dichroic filter mirror may be used. As in the examples described above, when it is desired that the optical imaging device 100 obtains a two-dimensional image of the inspection object using the illumination light, which is visible light, and the optical interference detector 200 obtains the optical interference data for obtaining a three-dimensional image of the inspection object using the measurement light, which is near-infrared light, it is possible to individually control the light paths of two lights having different wavelengths using the dichroic filter mirror. Therefore, when the property of the illumination light used in the optical imaging device 100 is in the non-visible light range, when an optical image to be obtained by the optical imaging device 100 is changed, or when the property of the measurement light used for obtaining optical interference data in the optical interference detector 200 is changed, suitable optical components may be used instead.

The light guide 300 may include a magnification changer 320. The magnification changer 320 is a component for changing the magnification of an image to be captured. As the magnification changer 320, a plurality of mutually exchangeable objective lenses having fixed magnifications may be disposed, and it is possible to obtain an enlarged image for an inspection object by changing the lenses. Alternatively, a single variable magnification objective lens having variable magnification may be used as the magnification changer 320. FIG. 3 illustrates, for example, a structure in which respective objective lenses are disposed on a rotary plate. However, other equivalent structures, in which a plurality of mutually exchangeable lenses is arranged, may be used. Alternatively, a single variable magnification objective lens may be disposed at the lower end of the light path controller 310. When the illumination light 115 and the measurement light 215 have to be projected with different optical axes as described above, multiple sets of the respective lenses of the magnification changer may also be arranged.

Figure 6:
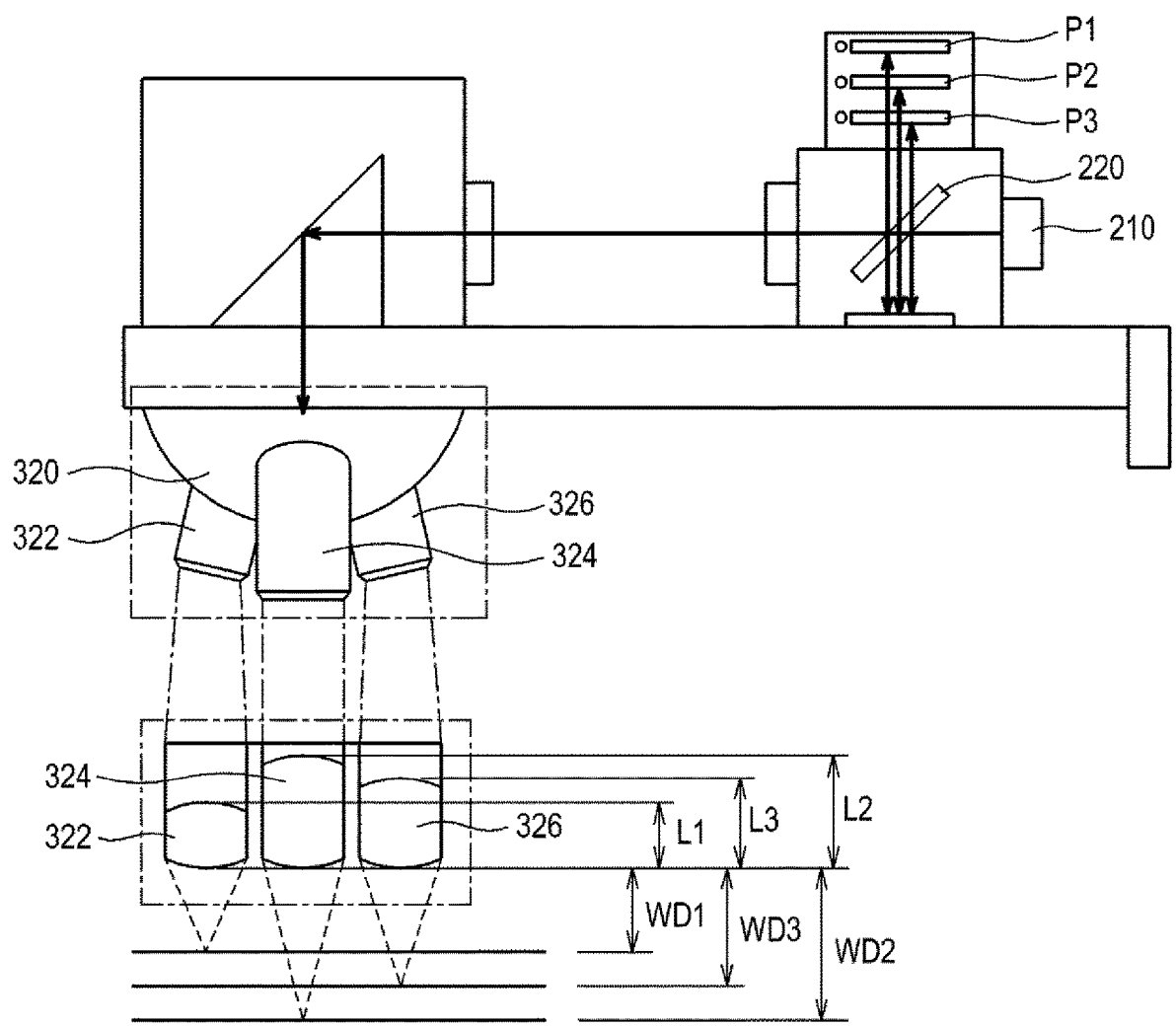
FIG. 6 illustrates a manner in which the optical interference detector operates according to the operation of a magnification changer in the biological tissue inspection apparatus according to the present disclosure.

When the magnification changer 320 changes the magnification, the position of the reference mirror 230 of the optical interference detector 200 may have to be changed depending on the characteristics of the lenses, for example, the thickness and the focal length of the lenses. FIG. 6 illustrates the principle that the reference mirror 230 has to move when a plurality of fixed magnification objective lenses 322, 324, and 326 is used. The optical interference data obtained by the optical interference detector 200 may be obtained from the interference caused due to the light path difference between the measurement light 215 and the reference light 225. At that time, depending on the thickness of the lenses used in the magnification changer 320, a path difference of the light paths may additionally occur. That is, when the thicknesses of the lenses (L1, L2, L3) are different, the distance of the free space, through which the measurement light passes, and the focal lengths of the lenses are changed together (WD1, WD2, WD3). Thus, a path difference that the measurement light 215 undergoes is additionally generated. Therefore, in order to sense the interference between the measurement light 215 and the reference light 225 by reflecting the path difference changed in this way, it is necessary to change the light path that the reference light 225 undergoes to be suitable for the change of the light path that the measurement light 215 undergoes according to the change of lenses. For this purpose, the position of the reference mirror may be changed (P1, P2, P3).

Figure 7:
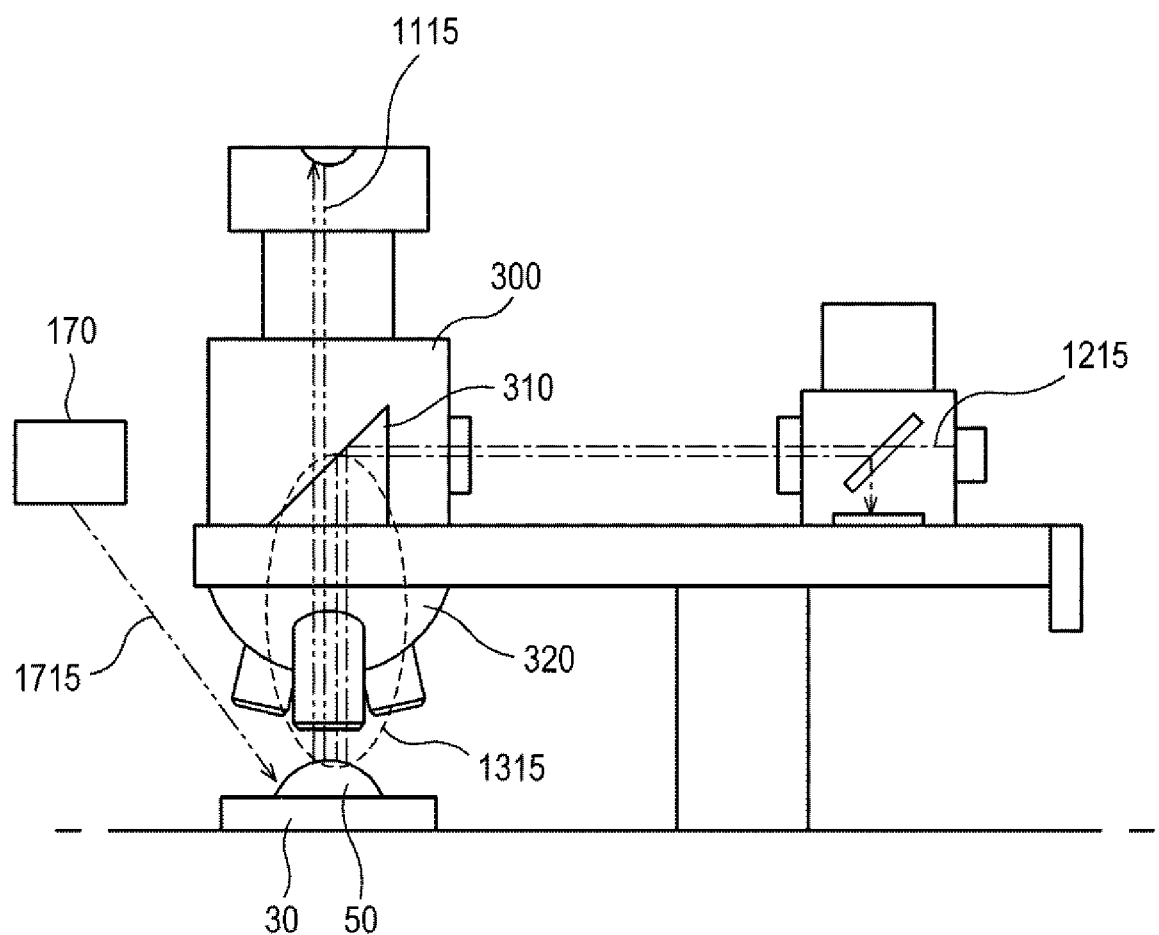
FIG. 7 illustrates the configuration of a light path formed in the biological tissue inspection apparatus according to the present disclosure.

Hereinafter, a description will be made regarding the formation of a first light path in which the light guide 300 guides the illumination light 115 from the optical imaging device 100 and the measurement light 215 from the optical interference detector 200 to the inspection object. FIG. 7 illustrates a configuration in which the illumination light 115 from the optical imaging device 100 is projected onto the inspection object 50 through the first light path 1115 by the light guide 300. The illumination light 115 for obtaining an optical image follows the first light path 1115. That is, the illumination light is first emitted from the illumination light source 110 and is incident on the light guide 300 via the beam splitter 130. The illumination light 115 incident on the light guide 300 passes through the light path controller 310 of the light guide 300 and is then projected onto the inspection object via the magnification changer 320. The illumination light 115 projected onto the inspection object 50 is reflected from the inspection object 50 so as to be directed to the optical imaging device, thereby forming the first light path 1115.

Meanwhile, the first light path 1115 of the illumination light described above is merely an example, and a person of ordinary skill in the art can adopt other methods for projecting illumination light. For example, the illumination light may be projected onto the inspection object 50 from another illumination source 170 at a different position through another light path 1715. In this case, the illumination light following the different light path 1715 may be directly projected onto the inspection object 50 without passing through the light guide 300. Even in this case, the illumination light projected onto the inspection object 50 through the other light path 1715 is reflected from the inspection object and passes through the light guide 300 along the same path as the first light path 1115 so as to be directed to the optical imaging device 100.

The measurement light 215 from the optical interference detector 200 may be guided to the inspection object 50 by the light guide 300 along a second light path 1215. As described above, the light emitted from the interference light source 210 is separated at the beam splitter 220, and the measurement light 215 passing through the beam splitter 220 is incident on the light path controller 310 of the light guide 300. The light path controller 310 changes the path of the measurement light 215 so as to direct the measurement light to the inspection object 50.

The first light path 1115 for obtaining an optical image and the second light path 1215 for obtaining optical interference data share a section 1315 by means of the light path controller 310 of the light guide 300. That is, as illustrated in FIG. 7, the light path between the light path controller 310 and the inspection object 50 in the first light path 1115 for obtaining an optical image, and the light path between the light path controller 310 and the inspection object 50 in the second light path 1215 for obtaining optical interference data overlap with each other. Alternatively, the light guide 300 may guide the illumination light 115 and the measurement light 215 to be projected onto the inspection object with different optical axes, instead of guiding the illumination light 115 and the measurement light 215 to be projected coaxially as described above. Since the Field Of View (FOV) of the optical imaging device 100 is wide and the FOV of the optical interference detector 200 is narrower than the FOV of the optical imaging device 100, it is necessary to project light with different optical axes when it is desired to perform a measurement with the optical interference detector 200 of various portions of an optical image obtained by the optical imaging device 100 with respect to the inspection object. Specifically, the light guide 300 may guide the measurement light 215 so as to obtain optical interference data for an area selected by the user through the area selector 40.

Guide Beam Projector

Figure 8:
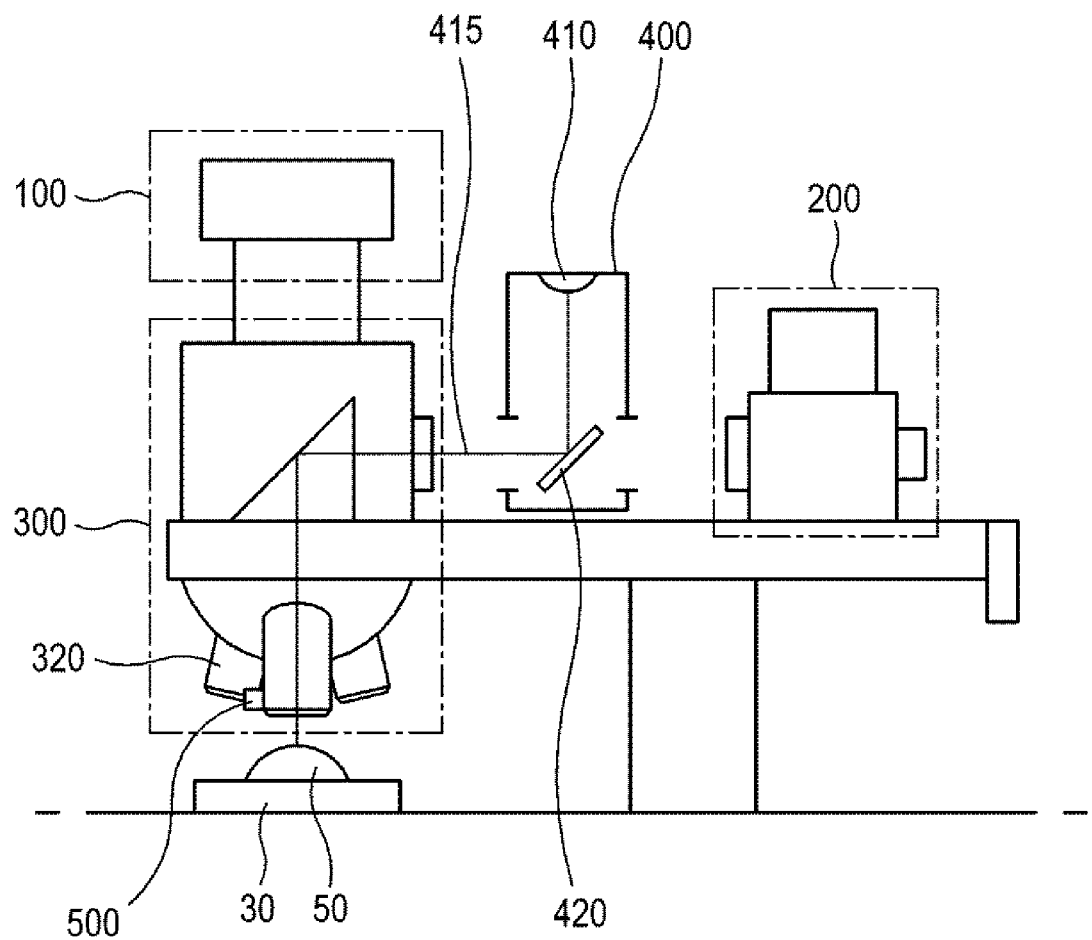
FIG. 8 illustrates the configuration and operation of a guide beam projector of the biological tissue inspection device according to the present disclosure.

As illustrated in FIG. 8, a guide beam projector 400 may be additionally disposed in the biological tissue inspection apparatus 10. The guide beam projector 400 may be disposed together with the optical imaging device 100 or the optical interference detector 200, or may be disposed at another position of the probe 20. Hereinafter, a description will be made regarding a case where the guide beam projector 400 is disposed together with the optical interference detector 200 for ease of explanation.

The guide beam projector 400 may include a guide beam light source 410 and a beam splitter 420, and project a guide beam 415 coaxially with the measurement light of the optical interference detector 200. The guide beam projector 400 projects the guide beam so as to assist a user such that the user is capable of determining an area where the optical interference data is being obtained. That is, since the measurement light 215 used for obtaining optical interference data is laser light in the infrared or near-infrared range, it is impossible to determine with the naked eye about which portion of the inspection object optical interference data is being obtained. Therefore, by projecting the guide beam 415 corresponding to the visible light range coaxially with the measurement light onto the inspection object, the user can determine an area of the inspection object, where the optical interference data is currently being obtained. A component such as the beam splitter 420 can be added to the inspection apparatus for the guide beam 415 to be projected coaxially with the measurement light 215. For example, the guide beam 415 may be projected onto a specific area of the inspection object, selected by the user through the area selector 40, so as to indicate that the optical interference data is being obtained for the area selected by the user. If necessary, the guide beam 415 may not be projected coaxially with the measurement light 215.

Distance Measurement Device

A distance measurement device 500 may be disposed at one end of the probe 30, specifically, at the end of the light guide 300, more specifically, together with the magnification changer 320. The distance measurement device 500 is capable of measuring the distance between the surface of the inspection object 50 from the magnification changer 320. The distance measurement device 500 may use an infrared ray, an ultrasonic wave, a laser, or the like in order to measure the distance. The distance measured by the distance measurement device 500 may be used in order to solve the problem that the measurement in the z-axis direction is not performed correctly when the optical interference detector 200 obtains optical interference data of the inspection object 50. Details will be described later.

Area Selector and Transceiver

As described above, the biological tissue inspection apparatus of the present disclosure may allow a user to obtain optical interference data for a desired area with respect to the optical image of the inspection object, which has been obtained by the optical imaging device 100. For this purpose, the biological tissue inspection apparatus of the present disclosure may further include the area selector 40. The area selector 40 may include a display 42 configured to display an optical image obtained by the optical imaging device 100 and an input device 44 configured to receive a user input so that a specific area of the optical image displayed on the display 42 can be selected. Conventional techniques may be utilized for the specific configurations of the display and the input device.

The biological tissue inspection apparatus 10 of the present disclosure may further include a transceiver 70. Although the present disclosure is proposed to perform biological tissue inspection quickly during surgery, in some cases it may be necessary to conduct a real-time inspection of the same tissue in a pathology department of a hospital as well, in order to improve the accuracy of the inspection. In order to perform such an inspection, the biological tissue inspection apparatus may transmit and receive, through the transceiver, an obtained optical image and optical interference data, or three-dimensional image data generated from the obtained optical image and the optical interference data, and other patient-related data, in real time during surgery.

Biological Tissue Inspection Method

A biological tissue inspection method according to the present disclosure will be described with reference to FIG. 9.

The inspection object 50, which is a sample taken from human tissue, may be loaded on the stage 30. The optical imaging device 100 can obtain an optical image of the inspection object 50. The optical interference detector 200 can obtain optical interference data for an area of the inspection object corresponding to all or part of the optical image. Since the FOVs of the optical imaging device 100 and the optical interference detector 200 are limited and there is a problem that accurate optical interference data cannot be obtained due to a step on the surface of the inspection object 50, the stage 30 is movable in the x-axis, y-axis, and z-axis directions in order to solve these problems.

Figure 9:
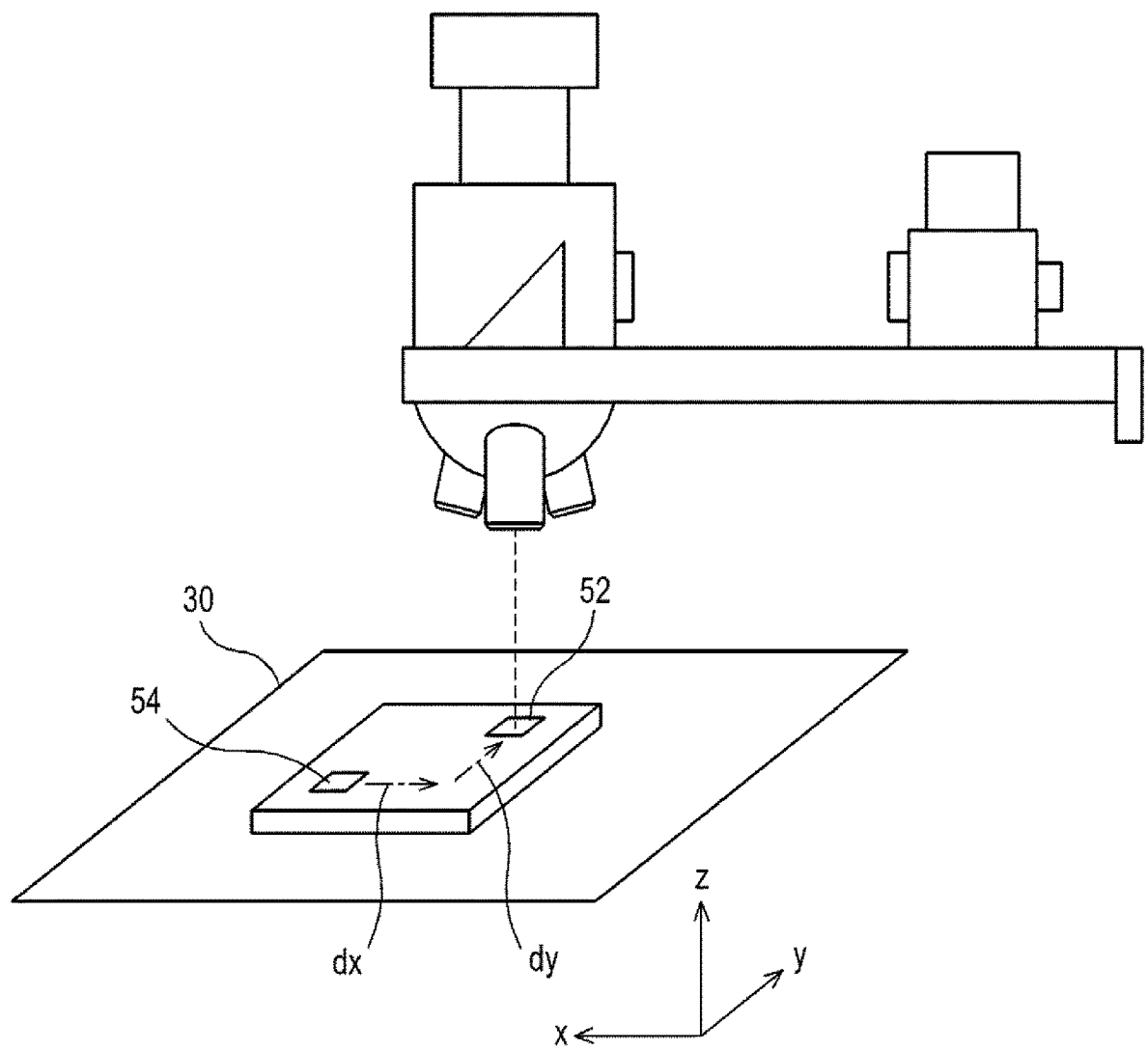
FIG. 9 illustrates the movement of a stage of the biological tissue inspection apparatus according to the present disclosure in x-axis and y-axis directions.

For example, as illustrated in FIG. 9, the inspection object 50 is loaded on the stage 30, and in order to move an area 54, from which a three-dimensional image of the inspection object 50 is desired to be obtained, into the FOV 52 of the current optical interference detector, it is possible to move the stage 30 in the x-axis and y-axis directions by dx and dy. The movement in the x-axis and y-axis directions as described above may be performed based on an optical image obtained by the optical imaging device 100 or the interference signal obtained by the optical interference detector 200. For example, when it is desired to perform an inspection using a three-dimensional image with respect to a specific area selected by the user from the optical image, the stage 30 can move in the x-axis and y-axis directions such that an area corresponding to the selected area of the inspection object is included in the FOV of the optical interference detector 200. On the other hand, an area of the inspection object included in the FOV may equally be changed by moving the probe 20 without moving the stage 30.

On the other hand, when a step on the surface of the inspection object 50 is large, a distortion in the optical interference data obtained for generating the three-dimensional image with respect to the inspection object 50 may occur. The depth to which the measurement light can penetrate from the surface of the inspection object 50 is several millimeters from the surface due to factors such as characteristics of the measurement light, the frequency of the measurement light, and characteristics of the lens of the optical system. When this range of several millimeters is defined as a "measurement range in the z-axis direction" of the optical interference detector, the step present on the surface of the inspection object 50 may fall outside the measurement range in the z-axis direction of the optical interference detector. In other words, a step may exist on the surface of the inspection object 50, and the difference between the high area and the low area of the step on the surface may be larger than the measurement range in the z-axis direction. In this case, when compared with the optical interference data obtained from the reflected light of the measurement light, which has been reflected from the high area of the surface of the inspection object 50, or from the back-scattered light of the measurement light, which has penetrated the surface of the high area to an area under the surface and has been scattered back, the optical interference data obtained from the reflected light of the measurement light, which has been reflected from the low area, and the back-scattered light of the measurement light, which has penetrated the surface of the low area to an area under the surface and has been scattered back, may appear in distorted form. Therefore, it is necessary to shift the position of the inspection object 50 in the z-axis direction in order to prevent the occurrence of such distorted data, or to remove the distorted data and obtain accurate data.

Figure 10:
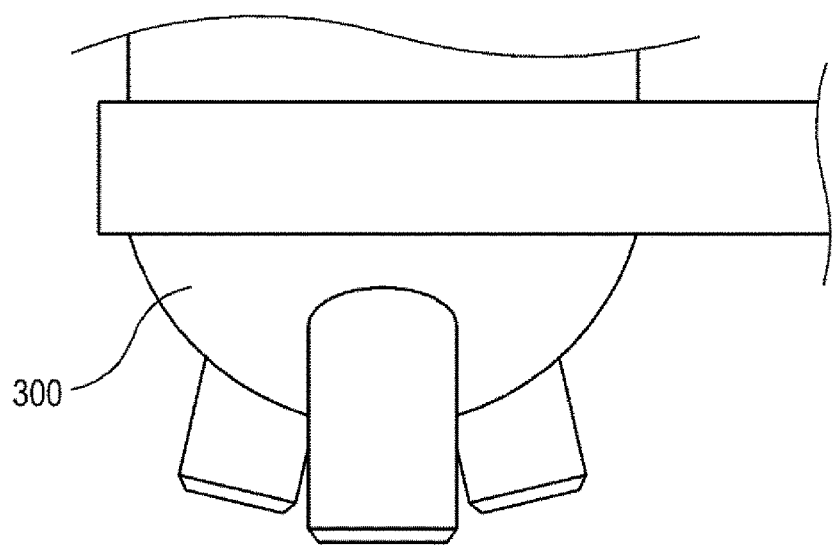
FIG. 10 illustrates the movement of the stage of the biological tissue inspection apparatus according to the present disclosure in a z-axis direction.
Figure 10:
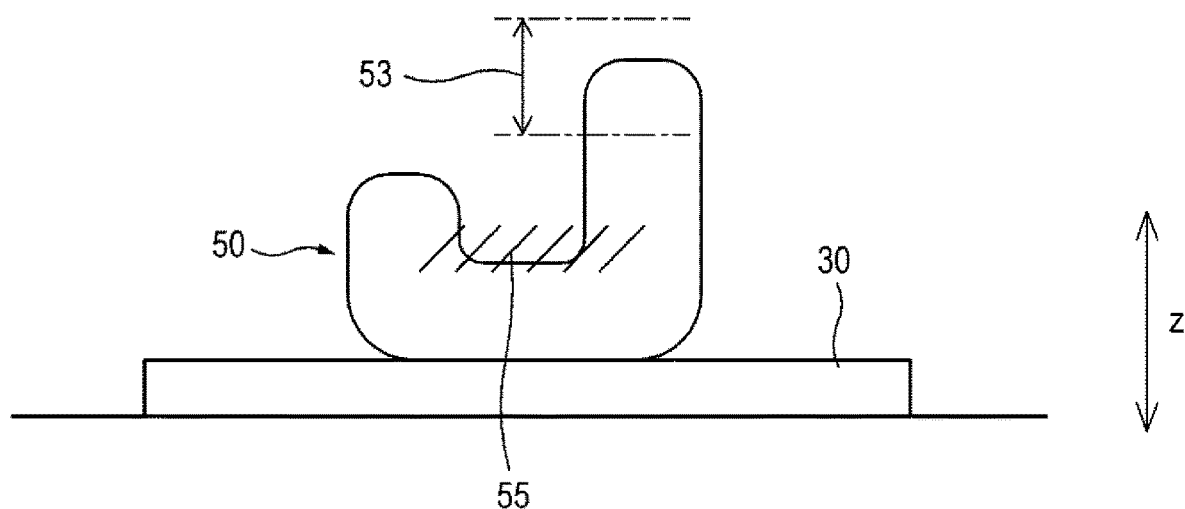

With reference to FIG. 10 in this regard, when there is a step on the surface of the measurement object 50 and the surface of an area 55 to be measured falls outside a measurement range 53 in the z-axis direction, the stage 30 or the probe 20 can be moved in the z-axis direction in order to measure the corresponding area. One method is to obtain optical interference data again for an area where it is determined that the optical interference data may be distorted due to a step on the surface, after having obtained all optical interference data for the inspection object 50 first. That is, one method is to obtain optical interference data again, after the stage 30 or the probe 20 is moved in the z-axis direction and the surface of the area where the optical interference data is determined to be distorted is included in the z-axis direction measurement range. Another method is to move the stage or the probe in real time in the z-axis direction while measuring the height on the surface of the inspection object when obtaining optical interference data for the inspection object 50 such that the surface of the inspection object is always included in the measurement range in the z-axis direction.

When the stage 30 or the probe 20 is moved in the z-axis direction, the width of movement of the stage 30 or the probe 20 may be automatically controlled based on the distance between the lens of the magnification changer 320 and the inspection object 50, which distance is measured by the distance measurement device 500. Alternatively, the stage 30 or the probe 20 may include a controller that can be operated by a user. When the user operates the controller, the stage 30 or the probe 20 may be moved in the z-axis direction. This configuration can be used for other purposes, rather than to include the surface of the inspection object in the above-described measurement range in the z-axis direction. For example, when the optical imaging device 100 is configured to obtain a two-dimensional image of the inspection object, the user may move the stage 30 or the probe 20 by operating the controller in order to focus a two-dimensional image while viewing the two-dimensional image.

In the embodiment disclosed above, as illustrated in FIG. 1, the biological tissue inspection apparatus according to the present disclosure is provided with a configuration in which the optical imaging device 100 is positioned at the upper side of the stage 30 in the vertical direction and the optical interference detector 200 is disposed on a side of the light guide 300. In this configuration, the path of the measurement light 215 from the optical interference detector 200 is changed by the light path controller 310 of the light guide 300. However, this configuration is merely an example, and it will be obvious to a person of ordinary skill in the art that the optical imaging device 100, the optical interference detector 200, and the light guide 300 may be used to perform the same function as the inspection apparatus of the present disclosure even if the arrangement of the optical imaging device 100, the optical interference detector 200, and the light guide 300 is different from that in the above-described embodiment. For example, the optical interference detector 200 may be disposed vertically above the light guide 300, and the optical imaging device 100 may be disposed on a side of the light guide 300. Alternatively, the optical imaging device 100 and the optical interference detector 200 may both be located at the upper side of the light guide 300. In this case, the light path controller 310 may be provided with a single beam splitter or dichroic filter mirror, a plurality of beam splitters or dichroic filter mirrors, or a combination thereof so as to guide illumination light and measurement light toward the inspection object, thereby performing the same function as the inspection apparatus in the previous embodiment.

A three-dimensional image generated by processing an optical image and optical interference data may be displayed through the display 60. The user can inspect and determine, for example, what kind of tissue the target area corresponds to and what condition the target area is in from the image displayed on the display, and can plan or proceed with a subsequent surgical procedure.

Figure 11:
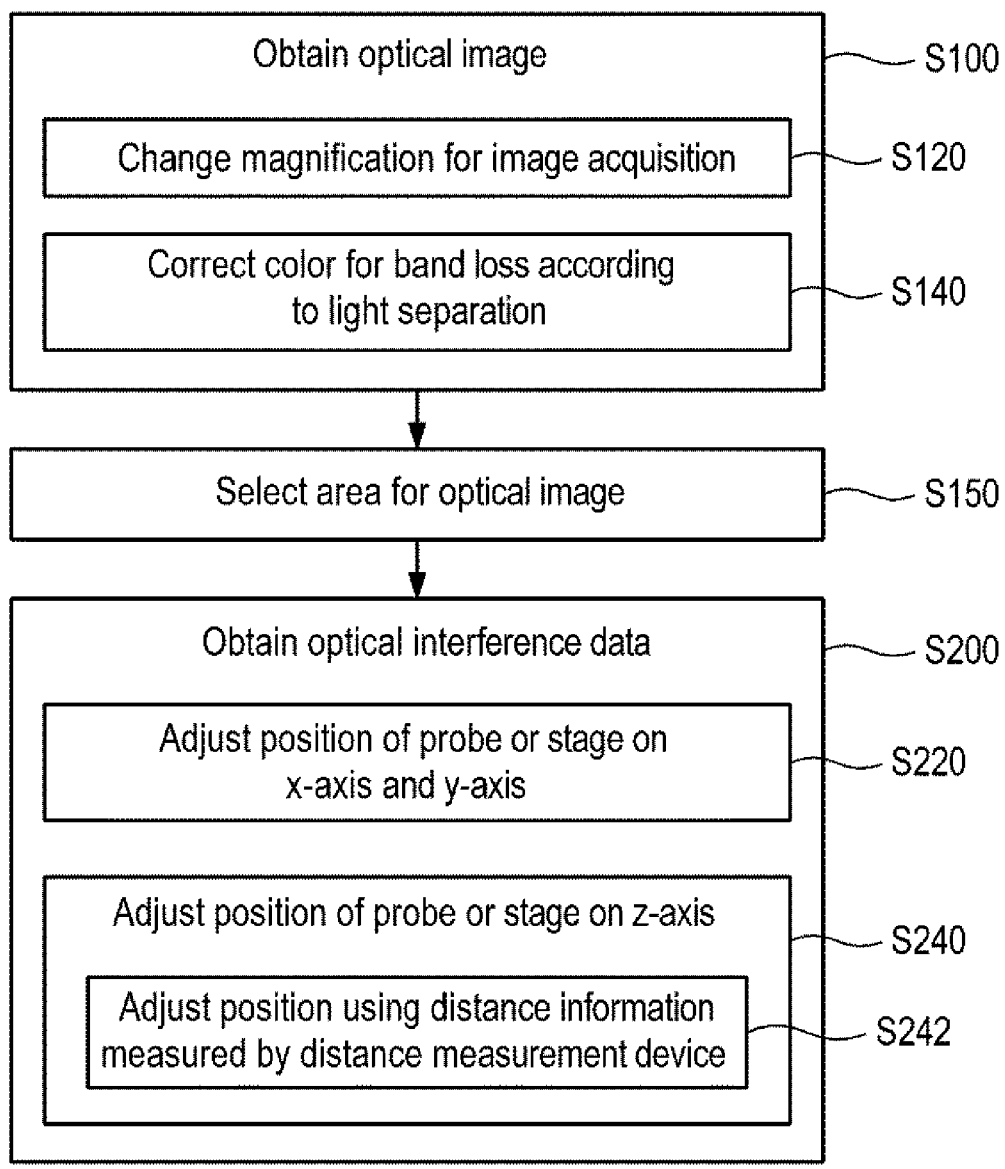
FIG. 11 illustrates a biological tissue inspection method according to the present disclosure.

FIG. 11 illustrates a sequence of an inspection method using the biological tissue inspection apparatus according to the present disclosure. The biological tissue inspection method according to the present disclosure includes obtaining an optical image by the optical imaging device 100 (S100) and obtaining optical interference data by the optical interference detector 200 (S200). In addition, after the obtaining the optical image, selecting, by a user, an area where it is desired to obtain optical interference data (S150) may be performed prior to the obtaining the optical interference data. As described above with regard to the biological tissue inspection apparatus, prior to the obtaining the optical image and the optical interference signal, adjusting the position of the probe 20 or the stage 30 on the x-axis, y-axis, and z-axis such that an area to be inspected of the inspection object is included within the FOVs of the optical imaging device 100 and the optical interference detector 200 (S220, S240) may be further included. Specifically, adjusting a position on the z-axis may be performed using distance information between the probe 20 and the inspection object 50, which has been separately measured via the distance measurement device 500 as described above (S242).

Meanwhile, before the obtaining the optical image, changing the magnification for obtaining the optical image may be further included (S120). Alternatively, although not illustrated, it is also possible to change the magnification prior to the obtaining the optical interference data and after the obtaining the optical image in order to make the magnification at the time of obtaining the optical image and the magnification at the time of generating the optical interference data different from each other. In this case, when obtained and measured images are displayed on the display as described above, indications showing magnification differences may be provided, or images having different magnifications may be displayed as images having the same magnification by processing the images having different magnifications. The light path controller 310 of the light guide 300 may separate the measurement light 215, the guide beam 415, and the illumination light 115, which have been reflected from the inspection object. Here, in the process of separating the guide beam 415 belonging to the visible light range, part of the wavelengths of the illumination light 215 belonging to the visible light range may also be removed. Therefore, in the measuring of the two-dimensional image, a color correction may be additionally performed on the optical image in order to restore the removal of part of the wavelengths described above (S140).

The biological tissue inspection method according to the present disclosure may be performed by being stored on a machine-readable or computer-readable storage medium as program instructions. The program instructions may include program instructions that implement the operations of the optical imaging device, the optical interference detector, the probe, and the stage. The program may be executed by a computer or a processor included in the biological tissue inspection apparatus according to the present disclosure, and may also be executed through a server or a computer at a remote place, which is communicably connected to the biological tissue inspection apparatus according to the present disclosure. A method of performing the biological tissue inspection method according to the present disclosure via a server or a computer at a remote place may be performed in a manner in which the server or computer at the remote place transmits corresponding instructions to the biological tissue inspection apparatus, the biological tissue inspection apparatus transmits a result obtained by performing the biological tissue inspection method according to the instructions to the server or computer at the remote place, and the server or computer at the remote place interprets the result again and transmits additional instructions to the biological tissue inspection apparatus.

While the present disclosure has been described and exemplified with reference to embodiments of the present disclosure, it will be understood by a person of ordinary skill in the art that various changes and modifications can be made without departing from the subject matter and the scope of the appended claims.

(Description of Reference Numerals) 10: biological tissue inspection apparatus, 20: probe, 30: stage, 100: optical imaging device, 200: optical interference detector, 300: light guide, 400: guide beam projector, 500: distance measurement device

What is claimed is:

1. An apparatus comprising:
a stage on which an inspection object is loaded; and
a probe configured to
obtain an optical image of the inspection object; and
obtain optical interference data about the inspection object of an area that is selected from the optical image,
wherein the probe or the stage is movable to obtain the optical interference data about the inspection object of the selected area,
wherein the probe includes:
an optical imaging device configured to obtain the optical image;
an optical interference detector configured to obtain the optical interference data; and
a light guide including a magnification changer and configured to
form a first light path along which illumination light is emitted from an illumination light source, reflected from the inspection object, and guided to the optical imaging device to obtain the optical image; and
form a second light path by causing measurement light to be incident on the inspection object to obtain the optical interference data,
wherein the magnification changer includes a plurality of fixed magnification objective lenses,
wherein the first light path and the second light path pass through one of the plurality of the fixed magnification objective lenses,
wherein the probe further includes a guide beam projector configured to project a guide beam such that a projection point of the guide beam is located within a Field Of View (FOV) of the optical imaging device, and
wherein a position of the probe or the stage is adjustable on a z-axis such that a surface of the inspection object is located within a measurement range in a z-axis direction of the optical interference detector.

2. The apparatus of claim 1, wherein the illumination light source is provided in the probe.

3. The apparatus of claim 1, wherein the illumination light source is provided outside the probe separately from the probe.

4. The apparatus of claim 1, wherein the light guide includes a light path controller, and
wherein the first light path and the second light path coaxially overlap with each other in a section between the light path controller and the inspection object.

5. The apparatus of claim 4, wherein the light path controller is a semi-transmissive mirror, and
wherein the semi-transmissive mirror allows the illumination light to pass therethrough and refracts the measurement light, or refracts the illumination light and reflects the measurement light.

6. The apparatus of claim 1, wherein the optical interference detector further includes:
an interference light source configured to project near-infrared light;
a beam splitter for optical interference measurement configured to separate the near-infrared light from the interference light source into the measurement light and reference light; and
a reference mirror configured to reflect the reference light.

7. The apparatus of claim 6, wherein the reference mirror is configured to move based on a thickness of the one of the fixed magnification objective lenses through which the second light path passes.

8. The apparatus of claim 1,
wherein the optical imaging device obtains the optical image such that the projection point of the guide beam is visually identified in the optical image, and
wherein the projection point of the guide beam is included in the selected area.

9. The apparatus of claim 8, wherein the guide beam projector projects the guide beam along the second light path.

10. The apparatus of claim 1, wherein the position of the probe or the stage is adjusted on the z-axis after the optical interference detector obtains the optical interference data of the inspection object in the selected area.

11. The apparatus of claim 1, wherein the position of the probe or the stage is adjusted on the z-axis simultaneously with the optical interference detector obtaining the optical interference data of the inspection object in the selected area.

12. The apparatus of claim 1, wherein the probe further includes a distance measurement device configured to measure a distance between the probe and the surface of the inspection object, and
wherein the position of the probe or the stage on the z-axis is adjusted based on the distance measured by the distance measurement device.

13. The apparatus of claim 1, wherein a position of the probe or the stage is adjustable on a x-axis, on a y-axis, or on the x-axis and the y-axis such that the selected area is included within the FOV of the optical imaging device or a FOV of the optical interference detector.

14. The apparatus of claim 1, further comprising:
a display configured to display the optical image; and
an input device configured to receive a user selection for selecting a partial area of the optical image.

15. The apparatus of claim 1, further comprising a transceiver configured to send out the optical image, the optical interference data, or the optical image and the optical interference data such that the optical image, the optical interference data, or the optical image and the optical interference data is to be shared in real time.

16. A method using an apparatus including a stage and a probe,
wherein the probe includes:
an optical imaging device configured to obtain an optical image;
an optical interference detector configured to obtain optical interference data; and
a light guide including a magnification changer including a plurality of fixed magnification objective lenses;
the method comprising the steps of:
changing a magnification for the probe to obtain an optical image or optical interference data;
forming, by the light guide, a first light path along which illumination light is emitted from an illumination light source, reflected from an inspection object, and guided to the optical imaging device;
obtaining, by the optical imaging device, the optical image of the inspection object;
selecting an area of the optical image;
forming, by the light guide, a second light path by causing measurement light to be incident on the inspection object to obtain the optical interference data; and
obtaining, by the optical interference detector, the optical interference data about the inspection object of the selected area of the optical image,
wherein the probe or the stage is movable to obtain the optical interference data about the inspection object of the selected area,
wherein the magnification for the probe is changed by the magnification changer,
wherein the first light path and the second light path pass through one of the plurality of the fixed magnification objective lenses,
wherein the probe further includes a guide beam projector configured to project a guide beam such that a projection point of the guide beam is located within a Field Of View (FOV) of the optical imaging device, and
the method further comprises the step of adjusting a position of the probe or the stage on a z-axis such that a surface of the inspection object is located within a measurement range in a z-axis direction of the optical interference detector.

17. The method of claim 16, wherein the adjusting the position of the probe or the stage on the z-axis is performed after the obtaining the optical interference data about the inspection object of the selected area.

18. The method of claim 16, wherein the adjusting the position of the probe or the stage on the z-axis is performed simultaneously with the obtaining the optical interference data about the inspection object of the selected area.

19. The method of claim 16, further comprising the step of adjusting a position of the probe or the stage on a x-axis, a y-axis, or the x-axis and the y-axis such that the selected area is included within the FOV (Field of View) of the optical imaging device or a FOV of the optical interference detector.

20. The method of claim 16, further comprising the step of correcting a color of the optical image.

* * * * *